United States Patent
Pleshko et al.

(10) Patent No.: US 10,712,310 B2
(45) Date of Patent: Jul. 14, 2020

(54) PROTEIN QUANTIFICATION BY NEAR INFRARED SPECTRAL IMAGING

(71) Applicant: Temple University-Of The Commonwealth System of Higher Education, Philadelphia, PA (US)

(72) Inventors: Nancy Pleshko, Cherry Hill, NJ (US); Arash Hanifi, King of Prussia, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 105 days.

(21) Appl. No.: 16/071,568

(22) PCT Filed: Jan. 20, 2017

(86) PCT No.: PCT/US2017/014389
§ 371 (c)(1),
(2) Date: Jul. 20, 2018

(87) PCT Pub. No.: WO2017/127716
PCT Pub. Date: Jul. 27, 2017

(65) Prior Publication Data
US 2019/0033254 A1 Jan. 31, 2019

Related U.S. Application Data

(60) Provisional application No. 62/286,113, filed on Jan. 22, 2016.

(51) Int. Cl.
*C07K 1/00* (2006.01)
*G01N 21/00* (2006.01)
(Continued)

(52) U.S. Cl.
CPC ......... *G01N 27/44721* (2013.01); *C07K 1/26* (2013.01); *G01N 21/359* (2013.01);
(Continued)

(58) Field of Classification Search
CPC ........ C07K 1/26; G01N 21/359; G01N 27/26; G01N 27/447; G01N 27/44717; G01N 27/44721; G01N 27/4473
See application file for complete search history.

(56) References Cited

U.S. PATENT DOCUMENTS

| 8,975,375 B2 | 3/2015 | Sahin |
| 2008/0074646 A1 | 3/2008 | Archibald |
| 2014/0004533 A1 | 1/2014 | Siino, Jr. |

OTHER PUBLICATIONS

Baykal, D., et al., Nondestructive assessment of engineered cartilage constructs using near-infrared spectroscopy. Appl Spectrosc, 2010. 64(10): p. 1160-6.
(Continued)

*Primary Examiner* — Dani Fox
(74) *Attorney, Agent, or Firm* — Riverside Law LLP

(57) ABSTRACT

The present invention introduces a protein/peptide quantification method based on near infrared spectral imaging of protein gel bands obtained from gel electrophoresis methodologies. Spectral imaging is a fast and reliable method that is simple to use and easily applicable to several procedures. When proteins are separated through gel electrophoresis, the gel is imaged using a near infrared spectrometer and a standard curve is used to calculate the protein/peptide content based on its relative near infrared absorbance to standard proteins. Compared to other protein quantification techniques, the methods of the present invention quantifies the proteins separated by gel electrophoresis without the need for contrast reagents or for purifying protein out of the gel, shortening the processing time, reducing the number of
(Continued)

steps involved, and eliminating the need for additional chemicals.

23 Claims, 7 Drawing Sheets

(51) Int. Cl.
  *G01N 27/447*  (2006.01)
  *C07K 1/26*  (2006.01)
  *G01N 21/359*  (2014.01)
  *G01N 21/64*  (2006.01)
  *G01N 21/65*  (2006.01)

(52) U.S. Cl.
  CPC ......... *G01N 21/6428* (2013.01); *G01N 21/65* (2013.01); *G01N 27/44782* (2013.01); *G01N 2021/6439* (2013.01)

(56) References Cited

OTHER PUBLICATIONS

Berth, M., et al., The state of the art in the analysis of two-dimensional gel electrophoresis images. Appl Microbiol Biotechnol, 2007. 76(6): p. 1223-43.
Boskey, A. and N. Pleshko Camacho, FT-IR imaging of native and tissue-engineered bone and cartilage. Biomaterials, 2007. 28(15): p. 2465-78.
Bradford, M.M., A rapid and sensitive method for the quantitation of microgram quantities of protein utilizing the principle of protein-dye binding. Anal Biochem, 1976. 72: p. 248-54.
Burkitt, W.I., et al., Toward Systeme International d'Unite-traceable protein quantification: from amino acids to proteins. Anal Biochem, 2008. 376(2): p. 242-51.
Butt RH, Coorssen JR. Coomassie blue as a near-infrared fluorescent stain: A systematic comparison with Sypro Ruby for in-gel protein detection. Molecular & Cellular Proteomics. Dec. 1, 2013;12(12):3834-50.
Cen, H. and Y. He, Theory and application of near infrared reflectance spectroscopy in determination of food quality. Trends in Food Science & Technology, 2007. 18(2): p. 72-83.
Chan, J.K., J.W. Thompson, and T.A. Gill, Quantitative determination of protamines by coomassie blue G assay. Anal Biochem, 1995. 226(1): p. 191-3.
Chevallet, M., S. Luche, and T. Rabilloud, Silver staining of proteins in polyacrylamide gels. Nature protocols, 2006. 1(4): p. 1852-1858.
de Moreno, M.R., J.F. Smith, and R.V. Smith, Mechanism studies of coomassie blue and silver staining of proteins. J Pharm Sci, 1986. 75(9): p. 907-11.
Domon, B. and R. Aebersold, Mass spectrometry and protein analysis. Science, 2006. 312(5771): p. 212-7.
Durig, J.R. and D.J. Gerson, Historical survey of the infrared and Raman spectroscopic study of biological molecules, in Infrared and Raman Spectroscopy of Biological Molecules. 1979, Springer. p. 35-43.
Fountoulakis, M., J.F. Juranville, and M. Manneberg, Comparison of the Coomassie brilliant blue, bicinchoninic acid and Lowry quantitation assays, using non-glycosylated and glycosylated proteins. J Biochem Biophys Methods, 1992. 24(3-4): p. 265-74.
Gratzer, S. (1995). Determination of Protein by Near Infrared Reflectance (NIR) Spectroscopy. International Association for Cereal Science and Technology. Retrieved Sep. 21, 2015 from https://www.icc.or.at/publications/icc-standards/standards-overview/159-standard -method (1 page).
Groves, W.E., F.C. Davis, Jr., and B.H. Sells, Spectrophotometric determination of microgram quantities of protein without nucleic acid interference. Anal Biochem, 1968. 22(2): p. 195-210.
Hanifi, A., et al., Clinical outcome of autologous chondrocyte implantation is correlated with infrared spectroscopic imaging-derived parameters. Osteoarthritis Cartilage, 2012. 20(9): p. 988-96.
Homma, S., T. Fukunaga, and A. Kagaya, Influence of adipose tissue thickness on near infrared spectroscopic signal in the measurement of human muscle. Journal of Biomedical Optics, 1996. 1(4): p. 418-424.
Huang, H., et al., Near infrared spectroscopy for on/in-line monitoring of quality in foods and beverages: A review. Journal of Food Engineering, 2008. 87(3): p. 303-313.
Issaq, H. and T. Veenstra, Two-dimensional polyacrylamide gel electrophoresis (2D-PAGE): advances and perspectives. Biotechniques, 2008. 44(5): p. 697-8, 700.
Koenig, J.L. and M.K. Antoon, Recent applications of FT-IR spectroscopy to polymer systems. Applied optics, 1978. 17(9): p. 1374-1385.
Krumholz A, Shcherbakova DM, Xia J, Wang LV, Verkhusha VV. Multicontrast photoacoustic in vivo imaging using near-infrared fluorescent proteins. Scientific reports. Feb. 3, 2014;4:3939.
Kuipers, B.J. and H. Gruppen, Prediction of molar extinction coefficients of proteins and peptides using UV absorption of the constituent amino acids at 214 nm to enable quantitative reverse phase high-performance liquid chromatography-mass spectrometry analysis. J Agric Food Chem, 2007. 55(14): p. 5445-51.
Luo S, Wehr NB, Levine RL. Quantitation of protein on gels and blots by infrared fluorescence of Coomassie blue and Fast Green. Analytical biochemistry. Mar. 15, 2006;350(2):233-8.
Manley M. Near-infrared spectroscopy and hyperspectral imaging: non-destructive analysis of biological materials. Chemical Society Reviews. 2014;43(24):8200-14.
McGoverin, C.M., et al., Nondestructive Assessment of Engineered Cartilage Composition by Near Infrared Spectroscopy. Ann Biomed Eng, 2016. 44(3): p. 680-92.
Noble, J.E. and M.J. Bailey, Quantitation of protein. Methods Enzymol, 2009. 463: p. 73-95.
Noble, J.E., et al., A comparison of protein quantitation assays for biopharmaceutical applications. Mol Biotechnol, 2007. 37(2): p. 99-111.
Olson, B.J. and J. Markwell, Assays for determination of protein concentration. Curr Protoc Pharmacol, 2007. Appendix 3: p. 3A.
Padalkar, M.V., R.G. Spencer, and N. Pleshko, Near infrared spectroscopic evaluation of water in hyaline cartilage. Ann Biomed Eng, 2013. 41(11): p. 2426-36.
Palukuru, U.P., C.M. McGoverin, and N. Pleshko, Assessment of hyaline cartilage matrix composition using near infrared spectroscopy. Matrix Biol, 2014. 38: p. 3-11.
Palukuru, U.P., et al., Near infrared spectroscopic imaging assessment of cartilage composition: Validation with mid infrared imaging spectroscopy. Anal Chim Acta, 2016. 926: p. 79-87.
Prieto, N., et al., Application of near infrared reflectance spectroscopy to predict meat and meat products quality: A review. Meat Science, 2009. 83(2): p. 175-186.
Rabilloud, T., et al., Two-dimensional gel electrophoresis in proteomics: Past, present and future. J Proteomics, 2010. 73(11): p. 2064-77.
Schönbrodt T, Mohl S, Winter G, Reich G. NIR spectroscopy—a non-destructive analytical tool for protein quantification within lipid implants. Journal of controlled release. Aug. 28, 2006;114(2):261-7.
Shevchenko, A., et al., In-gel digestion for mass spectrometric characterization of proteins and proteomes. Nat Protoc, 2006. 1(6): p. 2856-60.
Simonian, M.H. and J.A. Smith, Spectrophotometric and colorimetric determination of protein concentration. Curr Protoc Mol Biol, 2006. Chapter 10: p. Unit 10 1A.
Sittampalam, G.S., et al., Evaluation of amino acid analysis as reference method to quantitate highly purified proteins. J Assoc Off Anal Chem, 1988. 71(4): p. 833-8.
Smith BJ. Quantification of proteins on polyacrylamide gels. In the protein protocols handbook 2002 (pp. 237-242). Humana Press.
Smith, B.J., Quantification of proteins on polyacrylamide gels (nonradioactive). Methods Mol Biol, 1994. 32: p. 107-11.
Walker, J.M., The bicinchoninic acid (BCA) assay for protein quantitation. Methods Mol Biol, 1994. 32: p. 5-8.

PROTEIN QUANTIFICATION BY NEAR INFRARED SPECTRAL IMAGING

CROSS-REFERENCE TO RELATED APPLICATIONS

This application is the U.S. national phase application filed under 35 U.S.C. § 371 claiming benefit to International Patent Application No. PCT/US17/14389, filed Jan. 20, 2017, which is entitled to priority under 35 U.S.C. § 119(e) to U.S. Provisional Patent Application No. 62/286,113, filed Jan. 22, 2016, the contents of which are each incorporated herein by reference in their entirety.

BACKGROUND OF THE INVENTION

Protein and peptide quantification is an important process required by thousands of laboratories, research and development departments, and industries for activities ranging from protein characterization to clinical diagnostic testing to drug dosing. There are several methods for evaluating protein and peptide content quantitatively and qualitatively and multiple factors to consider for each type of application, including the accuracy required, concentration of protein in the sample, assay specificity, presence of interfering chemicals in the solvents used and the ease and reliability of the assay method. Gel electrophoresis has been used for size-based separations of protein mixtures for over forty years, and is still the most frequently used technique for protein separations in many biological research laboratories. However, quantification of proteins separated by the gel method still has many challenges.

The fast-paced development of protein and peptide applications in therapeutic and non-therapeutic industries, in addition to great progress in proteomics methods, has increased the importance of developing an accurate methodology for quantifying proteins. There are several methods to measure individual proteins, either in solution or using a solid-phase assay such as a gel. However, each method has certain limitations.

Amino acid analysis is the most accurate available method for protein quantification. The procedure consists of several steps: hydrolysis, derivatization, separation, and detection followed by quantification. It is based on the measurement of individual amino acid content in the protein/peptide structure and the calculation of total protein using these individual measurements. However, this is a very expensive method that also requires long processing times, and the results are also greatly affected by the level of the operator's technical expertise. Detected protein content highly depends on the response of any given sequence to hydrolysis, derivatization conditions, or sample contaminants (such as the presence of nonvolatile amines like Tris or glycine). Therefore, there are few core facilities that perform amino acid analysis and usually laboratories do not run their own amino acid analysis equipment. In addition, this method must be performed on pure proteins, which would require extraction of proteins from the electrophoresis gels. Further, this is a destructive method of analysis.

The UV-visible absorbance method is usually used to determine the protein content in solutions containing a single type of protein or to calculate the total protein content of the solution. This is a nondestructive method, allowing the proteins to be recovered for further analysis. Aromatic amino acid residues (tyrosine and tryptophan) and peptide bonds absorb UV light and the absorbance at 280 nm is measured as an indicator of protein content. In this method, any protein solution can be analyzed and the precision is about 10-100 mg of protein. The UV spectrometer is inexpensive and easy to use, and can also be coupled with colorimetric methods to enhance accuracy. Colorimetric methods are based on the chemical binding of a dye to the protein sequence. There are different types of dye attachment, including protein-copper chelation (Bicinchoninic assay (BCA) and Lowry assay) and dye-binding based detection (Bradford and 660 Assay). The Bradford assay measures the degree of binding to Coomassie Brilliant Blue dye, which changes color from brown to blue in the presence of proteins. However, the UV absorbance method cannot be used on proteins separated by gel electrophoresis because gel material absorbs UV light over the same range of wavelengths. Additionally, proteins that do not contain aromatic amino acids cannot be quantified based on UV absorbance. Colorimetric assays are easy to use, but they are highly sensitive to sample components (such as detergents and reducing agents), protein composition, protein structure, and dye-binding properties. Therefore, the assays are semi-quantitative, and not as precise as gold standard methods such as amino acid analysis since protein absorbance at 280 nm depends on protein amino acid composition and secondary and tertiary protein structures. In addition, the assay outcome depends on the number of basic amino acid residues in the analyzed protein, which can vary greatly among proteins, and make interpretations of results challenging.

The mass spectrometry method uses excitation of protein/peptide ions by different sources, such as electron spray, and measures signal intensities across samples in a mass to charge (m/z) range. Because sample processing, separation, and transfer to the mass spectrometer are generally automated, quantitative data can only be obtained from liquid chromatography-mass spectrometry and liquid chromatography-tandem mass spectrometry experiments by determination of the abundance of different proteins from their mass spectra. Mass spectrometry is frequently used for functional proteomics, which seeks to measure small changes in protein abundance in a complex biological system in response to perturbations such as disease progression or drug treatment. Notwithstanding the sensitivity of the method, mass spectrometry is very expensive and slow, and expertise is required to run the mass spectrometer and interpret the results. Additionally, mass spectrometers may not be entirely quantitative. Mass spectrometry analysis also requires purified proteins separated by gels to be extracted, and it is a destructive technique.

Another method for protein quantification is based on image analysis of proteins directly on electrophoresis gels, which can be performed on a microscopic image of the gel to quantify the protein content. The method depends on the assumption that the protein bands are well resolved, requires the addition of an external contrast agent, and conversion of the microscopic images to digital data for analysis increases the processing error. Visual protein detection for gel electrophoresis ranges from 1 ng to 5 ng/band for silver stained gels and 40 ng to 50 ng/band for Coomassie Blue stained gels. This requires a very accurate calibration curve for the stain intensity to accompany the microscopic image of the gel, which can be user dependent for solutions with low protein content and includes low image resolution at the gel band edges, and thus further external contrast must be added to the protein.

Immunological based methods employ an antibody specific for a protein that are fixed on a polymeric substrate, and interaction of the protein sample with the antibody is analyzed. Usually the target protein is detected with a second antibody that recognizes a different epitope to the capture antibody. However, even if antibodies could be found to bind to every protein in the sample, the signal intensity for each antigen-antibody interaction would depend not only on the abundance of the target protein but also on the strength of the antigen-antibody binding, and it would be very difficult to quantify. This method also cannot be applied to protein bands on gel materials.

Recently, EMD Millipore has introduced The Direct Detect™ spectrometer that uses infrared-based methods in the mid-infrared spectral range for protein quantification in a solution. The process is very similar to the UV absorbance methods described herein, where a drop of protein solution is used to measure the total protein (or individual protein if the solution contains a single type of protein). However, this technology requires the use of a membrane comprising hydrophilic polytetrafluoroethylene (PTFE) that is transparent in the mid-infrared region, and is only applicable to measure total protein content of the solution, not individual proteins mixed in a solution. The Amide I infrared spectral region is used for quantification, but this spectral region is also sensitive to water content in the sample.

Overall, there is a need in the art for simpler, improved methods for more precise quantification of proteins and peptides that have been separated by gel electrophoresis, the method utilized most frequently in biological labs. The present invention meets this need.

SUMMARY OF THE INVENTION

The present invention provides a protein/peptide quantification method based on spectral imaging of protein gel bands present in gel electrophoresis methodologies. This method is based on the inherent contrast of the proteins from the vibrations of the molecules within the proteins, and does not require the addition of external contrast agents.

In one aspect, the invention relates to a method of quantifying protein in an electrophoresis gel. The method comprises the steps of: loading a sample including at least one protein into a gel via electrophoresis to generate at least one protein band; acquiring an infrared spectral dataset from the at least one protein band using near infrared spectral imaging (NIRSI); generating an infrared hyperspectral image from the infrared spectral dataset for each of the at least one protein band, the infrared hyperspectral image comprising a plurality of pixels; calculating the integrated area under at least one wavenumber of the infrared spectrum for every pixel in the infrared hyperspectral image; summing the calculated integrated area of every pixel in the infrared hyperspectral image for each of the at least one protein band; and quantifying the amount of protein in the at least one protein band by correlating the sum of the calculated integrated areas with a protein content calibration curve.

In one embodiment, the at least one wavenumber of the infrared spectrum comprises the range between 4600 cm$^{-1}$ and 4450 cm$^{-1}$. In one embodiment, the at least one wavenumber of the infrared spectrum is selected from 4020 cm$^{-1}$, 4050 cm$^{-1}$, 4260 cm$^{-1}$, 4310 cm$^{-1}$, 4526 cm$^{-1}$, and 4890 cm$^{-1}$. In one embodiment, the at least wavenumber of the infrared spectrum comprises a range centered at a wavenumber selected from 4020 cm$^{-1}$, 4050 cm$^{-1}$, 4260 cm$^{-1}$, 4310 cm$^{-1}$, 4526 cm$^{-1}$, and 4890 cm$^{-1}$. In one embodiment, the method comprises obtaining a first, second, third, or fourth derivative of the infrared spectrum.

In one embodiment, the protein content calibration curve is given by the equation $y=-2.253x^2+361.38x+655.82$, wherein y is the amount of protein in micrograms and x is the sum of the calculated area under the wavenumber range of the infrared spectra between 4600 cm$^{-1}$ and 4450 cm$^{-1}$ for each pixel of the infrared hyperspectral image acquired from each protein band. In one embodiment, the protein content calibration curve is given by the equation $y=-8.1636x^2+472.37x+485.35$, wherein y is the amount of protein in micrograms and x is the sum of the calculated area under the wavenumber range of the infrared spectra between 4600 cm$^{-1}$ and 4450 cm$^{-1}$ for each pixel of the infrared hyperspectral image acquired from each protein band.

In one embodiment, the protein content calibration curve is given by the equation $y=355.1 \ln(x)-764.13$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band. In one embodiment, the protein content calibration curve is given by the equation $y=363.12 \ln(x)-818.64$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band. In one embodiment, the protein content calibration curve is given by the equation $y=431.92 \ln(x)-950.24$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band.

In one embodiment, the electrophoresis gel is stained to visualize the at least one protein band using one of a Coomassie stain, a silver stain, a fluorescent stain, and a negative stain. In one embodiment, the sample of proteins further comprises a calibrant. In one embodiment, NIRSI is used with a spatial resolution between 1 and 1000 µm. In one embodiment, the infrared spectrum is recorded in a range between 12000 and 3000 cm$^{-1}$. In one embodiment, the infrared spectrum is recorded with a spectral resolution between 1 and 100 cm$^{-1}$. In one embodiment, NIRSI is performed by co-adding and averaging a plurality of scans to improve the signal-to-noise ratio.

In another aspect, the invention relates to a method of generating a protein content calibration curve. The method loading a plurality of protein samples, each sample having a known amount of protein, into a gel via electrophoresis to generate a protein band for each sample; acquiring an infrared spectral dataset from each of the protein bands using NIRSI; generating an infrared hyperspectral image from the infrared spectral dataset for each of the protein bands, the infrared hyperspectral image comprising a plurality of pixels; calculating the integrated area under at least one wavenumber of the infrared spectrum for every pixel in the infrared hyperspectral image; summing the calculated integrated area of every pixel in the infrared hyperspectral image for each of the protein bands; plotting the known amount of protein in each protein band against the sum of the calculated integrated area for each protein band; and generating a line or curve of best fit to create a protein content calibration curve.

In one embodiment, the at least one wavenumber of the infrared spectrum comprises the range between 4600 cm$^{-1}$ and 4450 cm$^{-1}$. In one embodiment, the at least one wavenumber of the infrared spectrum is selected from 4020 cm$^{-1}$, 4050 cm$^{-1}$, 4260 cm$^{-1}$, 4310 cm$^{-1}$, 4526 cm$^{-1}$, and 4890 cm$^{-1}$. In one embodiment, the at least wavenumber of the infrared spectrum comprises a range centered at a wavenumber selected from 4020 cm$^{-1}$, 4050 cm$^{-1}$, 4260 cm$^{-1}$, 4310 cm$^{-1}$, 4526 cm$^{-1}$, and 4890 cm$^{-1}$. In one embodiment, the method comprises obtaining a first, second, third, or fourth derivative of the infrared spectrum.

In another aspect, the invention relates to a near infrared spectral imaging device that automatically performs the methods of the present invention.

In one embodiment, the methods of the present invention are performed using Raman spectral imaging.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
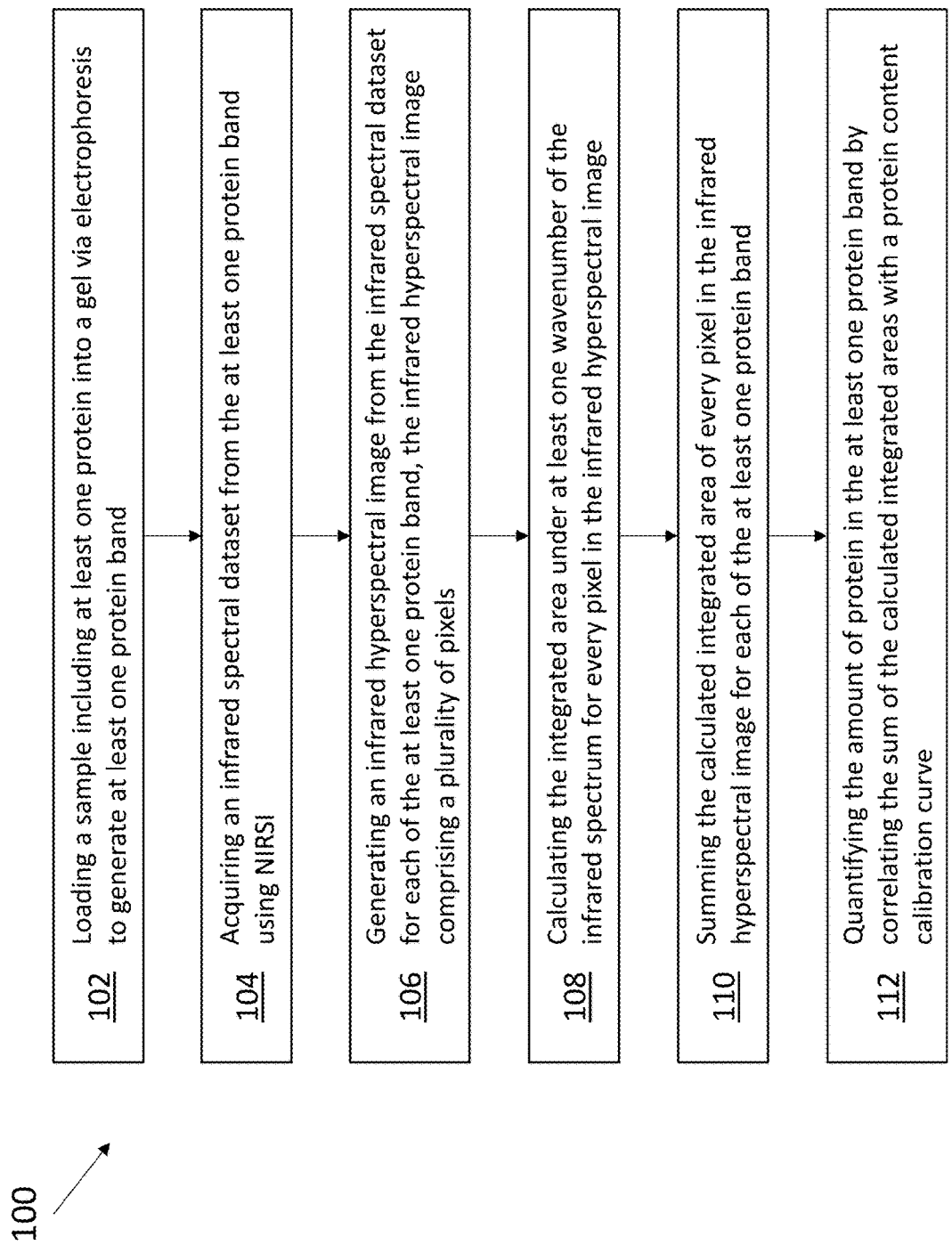
FIG. 1 depicts a flowchart illustrating an exemplary method of quantifying protein and peptides using near infrared spectral imaging.

The present invention introduces a protein/peptide quantification method based on spectral imaging of protein gel bands obtained from gel electrophoresis methodologies. Spectral imaging is a fast and reliable method that is simple to use and easily applicable to several procedures. When proteins are separated through gel electrophoresis, the gel is imaged using a spectrometer and a standard curve is used to calculate the protein/peptide content based on its relative absorbance to standard proteins. No external contrast is required, as the contrast is inherent from the vibrations of the molecular components of the proteins. Compared to other protein quantification techniques, the methods of the present invention quantifies the proteins separated by gel electrophoresis without the need for contrast reagents or for extracting purified protein out of the gel, shortening the processing time, reducing the number of steps involved, and eliminating the need for additional chemicals.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"Acquiring a near infrared dataset" is meant to encompass the steps of exposing a sample to radiation in the near infrared spectral range and detecting the near infrared radiation transmitted through, or reflected off of, the sample with a detector that is sensitive to radiation in the near infrared spectral range. The means of emitting and detecting near infrared radiation can by a near infrared imaging spectrometer, or any combination of a near infrared source and detector and other instrumentation that enables detection of near infrared radiation at specific frequencies transmitted through or reflected off of a sample.

The term "absorption peak area" or "absorption peak areas" as used herein, refers to one or more parts of an infrared absorption spectrum observed following the exposure of a sample to infrared (IR) radiation, as described herein. Once an infrared absorption spectrum is obtained using the IR based methods described herein, the area under one or more peaks in the spectrum is calculated by drawing a baseline across the peak and measuring the integrated area enclosed in the peak.

"Sample" or "biological sample" as used herein means a biological material from a subject, including but is not limited to organ, tissue, exosome, blood, plasma, saliva, urine and other body fluid. A sample can be any source of material obtained from a subject.

The term "wavelength," generally refers to the distance between one peak or crest of a wave and the next peak or crest. It is equal to the speed of the wave divided by its frequency, and to the speed of a wave times its period. Wavelength is a characteristic of both traveling waves and standing waves, as well as other spatial wave patterns. Wavelength is commonly designated by the Greek letter lambda (k). Assuming that a sinusoidal wave is moving at a fixed wave speed, wavelength is inversely proportional to the frequency of the wave. Therefore, waves with higher frequencies have shorter wavelengths, and waves with lower frequencies have longer wavelengths.

The term "wave number," is a property of a wave proportional to the reciprocal of its wavelength. It is generally measured in units of $cm^{-1}$ and can be defined by the number of wavelengths per unit distance, i.e., proportional to $1/\lambda$, where $\lambda$ is the wavelength. Wavenumbers presented in $cm^{-1}=10,000/\lambda(\mu m)$.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

The present invention provides devices, systems, and methods for quantifying proteins and peptides in electrophoresis gels using spectral imaging. The present invention represents an improvement over the prior art in protein/peptide quantification in a number of aspects, one of which is that it does not require additional treatment or processing steps for the electrophoresis gel.

The method is sensitive enough to detect protein content as low as 10 ng. Referring now to FIG. 1, an exemplary method 100 of using near infrared spectral imaging (NIRSI) to quantify proteins/peptides in an electrophoresis gel is presented. Method 100 begins with step 102, wherein a sample including at least one protein is loaded into a gel via electrophoresis to generate at least one protein band. The electrophoresis technique can be any suitable technique, including agarose gel electrophoresis and polyacrylamide gel electrophoresis. In step 104, NIRSI is used to acquire an infrared spectral dataset from the at least one protein band. In step 106, spectroscopic software is used to generate an infrared hyperspectral image from the infrared spectral dataset for each of the at least one protein band, wherein the infrared hyperspectral image comprises a plurality of pixels. In step 108, spectroscopic software is used to calculate the integrated area under at least one wavenumber of the infrared spectrum for every pixel in the infrared hyperspectral image. The at least one wavenumber of the infrared spectrum may be determined by the frequencies that arise from vibrations present in a protein structure, including but not limited to wavenumber ranges or peaks centered at 4020 $cm^{-1}$, 4050 $cm^{-1}$, 4260 $cm^{-1}$, 4310 $cm^{-1}$, 4526 $cm^{-1}$, and 4890 $cm^{-1}$. In some embodiments, the at least one wavenumber is the entire range between 4600 $cm^{-1}$ and 4450 $cm^{-1}$. In certain embodiments wherein a single wavenumber is used, the integrated area is the wavenumber peak. In certain embodiments wherein a range of wavenumbers is used, the integrated area is the area under the curve. In some embodiments, the infrared spectra may be processed to yield first, second, third, or fourth derivatives of the spectra for calculation of integrated area or peak heights. Those skilled in the art will understand that any suitable spectroscopic software capable of performing the aforementioned steps may be used. In step 110, the calculated integrated area of every pixel in the infrared hyperspectral image is summed for each of the at least one protein band. In step 112 the amount of protein in the at least one protein band is quantified by correlating the sum of the calculated integrated areas with a protein content calibration curve.

A protein content calibration curve may be presented as $y=f(x)$, where y is the amount of protein and $f(x)$ can be any suitable function, such as a linear function, a polynomial function, an algebraic function, a logarithmic function, and the like. In one embodiment, the protein content calibration curve is given by a first equation $y=-2.253x^2+361.38x+655.82$, wherein y is the amount of protein in µg and x is the sum of the calculated areas under the wavenumber range of the infrared spectra between 4600 $cm^{-1}$ and 4450 $cm^{-1}$ for each pixel of the infrared hyperspectral image acquired from each protein band. The first equation may be used to quantify protein contents in the 0 to 80 µg range. In another embodiment, the protein content calibration curve is given by a second equation $y=-8.1636x^2+472.37x+485.35$, wherein y is the amount of protein in µg and x is the sum of the calculated areas under the wavenumber range of the infrared spectra between 4600 $cm^{-1}$ and 4450 $cm^{-1}$ for each pixel of the infrared hyperspectral image acquired from each protein band. The second equation may be used to quantify protein content in the 0 to 20 µg range.

In another embodiment, the protein content calibration curve is given by a third equation $y=355.1 \ln(x)-764.13$, wherein y is the amount of protein in ng and x is the sum of the calculated area under the wavenumber range of the infrared spectra between 4600 $cm^{-1}$ and 4450 $cm^{-1}$ for each pixel of the infrared hyperspectral image acquired from each protein band. The third equation may be used to quantify bovine serum album (BSA) protein content in the 0 to 2000 ng range. In another embodiment, the protein content calibration curve is given by a fourth equation $y=363.12 \ln(x)-818.64$, wherein y is the amount of protein in ng and x is the sum of the calculated area under the wavenumber range of the infrared spectra between 4600 $cm^{-1}$ and 4450 $cm^{-1}$ for each pixel of the infrared hyperspectral image acquired from each protein band. The fourth equation may be used to quantify lysozyme protein content in the 0 to 2000 ng range. In another embodiment, the protein content calibration curve is given by a fifth equation $y=431.92 \ln(x)-950.24$, wherein y is the amount of protein in ng and x is the sum of the calculated area under the wavenumber range of the infrared spectra between 4600 $cm^{-1}$ and 4450 $cm^{-1}$ for each pixel of the infrared hyperspectral image acquired from each protein band. The fifth equation may be used to quantify IgG protein content in the 0 to 2000 ng range.

In some embodiments, NIRSI may be used to measure protein content of at least one protein band without generating a new calibration equation. For example, the equation used may be based on a preexisting standard curve generated from a sample set and gel other than the one being analyzed. Quantification in this method is faster but may be less accurate compared to the use of a calibration equation from a set of standards in the gel being analyzed.

In some embodiments, NIRSI acquires an infrared spectral dataset of an entire electrophoresis gel, with the at least one protein band visible in the infrared dataset. In other embodiments, the electrophoresis gel may be stained to visualize the at least one separated protein band. The stain can be any stain typically used in the art, including Coomassie stains, silver stains, fluorescent stains, and negative stains (such as zinc-based stains that stain the gel but not the protein bands). A staining step may be helpful for an operator to visualize protein bands prior to NIRSI data acquisition.

In another aspect, the present invention comprises a method of generating a protein content calibration curve. In general, a protein content calibration curve refers to a graphical display of the functional relationship between a value of an observed signal to a known protein sample amount. A protein calibration curve may be generated using a calibrant, which includes protein samples of known amounts. Typically, protein samples encompassing a range of known amounts are used as calibrants to generate a protein content curve.

Figure 2:
FIG. 2 depicts a flowchart illustrating an exemplary method of creating a protein content calibration curve using near infrared spectral imaging.

Referring now to FIG. 2, an exemplary method 200 of using NIRSI to generate a protein content calibration curve is depicted. Method 200 begins with step 202, wherein a plurality of protein samples, each sample having a known amount, is loaded into a gel via electrophoresis to generate a protein band for each sample. In step 204, NIRSI is used to acquire an infrared spectral dataset from each of the protein bands. In step 206, spectroscopic software is used to generate an infrared hyperspectral image from the infrared spectral dataset for each of the protein bands, wherein the infrared hyperspectral image comprises a plurality of pixels. In step 208, spectroscopic software is used to calculate the integrated area under at least one wavenumber of the infrared spectrum for every pixel in the infrared hyperspectral image. The at least one wavenumber of the infrared spectrum may be determined by the frequencies that arise from vibrations present in a protein structure, including but not limited to wavenumber ranges or peaks centered at 4020 $cm^{-1}$, 4050 $cm^{-1}$, 4260 $cm^{-1}$, 4310 $cm^{-1}$, 4526 $cm^{-1}$, and 4890 $cm^{-1}$. In some embodiments, the at least one wavenumber is the entire range between 4600 $cm^{-1}$ and 4450 $cm^{-1}$. In certain embodiments wherein a single wavenumber is used, the integrated area is the wavenumber peak. In certain embodiments wherein a range of wavenumbers is used, the integrated area is the area under the curve. In some embodiments, the infrared spectra may be processed to yield first, second, third, or fourth derivatives of the spectra for calculation of integrated area or peak heights. In step 210, calculated integrated area of every pixel in the infrared hyperspectral image is summed for each of the protein bands. In step 212, the known amount of protein in each protein band is plotted against the sum of the calculated integrated area for each protein band. In step 214, a line or curve of best fit is generated to create a protein content calibration curve.

In some embodiments, the calibrants are used within the methods of the present invention in advance, such that a protein content calibration curve is created prior to the quantification of protein samples having unknown amounts. In other embodiments, the calibrants can be run in parallel with protein samples having unknown amounts in an electrophoresis gel.

Without wishing to be bound by theory, it is contemplated that any suitable IR imaging instrument capable of reading spectra in the ranges provided elsewhere herein may be used in the methods according to the present invention. The NIRSI parameters used to acquire infrared spectra within the methods of the present invention can be any suitable parameters. For example, the spatial resolution of near IR spectral imaging can be between 1 and 1000 μm, such as 3, 6.25, 25, and 50 μm, depending on the instrumentation. The wavenumber range can be any suitable range, encompassing at least the range between 4600 $cm^{-1}$ to 4450 $cm^{-1}$, such as a broadband source range between 12000 and 3000 $cm^{-1}$. Further, near infrared absorbances from proteins other than that centered at 4526 $cm^{-1}$ can be used for calibration and quantification, such as those centered at about 4020 $cm^{-1}$, 4050 $cm^{-1}$, 4260 $cm^{-1}$, 4310 $cm^{-1}$, and 4890 $cm^{-1}$. The spectrometer can also be laser-based on one wavelength (wavenumber) for increased speed of data acquisition and decreased costs. The spectral resolution can be chosen based on the wavenumber range or to suit the operator, and can be between 1 and 100 $cm^{-1}$, or typically between 2 and 16 $cm^{-1}$. In various embodiments, the collection of spectral imaging data can comprise the averaging of co-added scans to improve the signal-to-noise ratio. Persons skilled in the art will understand that the NIRSI parameters may be adjusted within reasonable ranges to improve the accuracy of measurements.

As contemplated herein, the present invention includes a system platform for performing the data gathering and interpretation aspects of the methods for quantifying protein and peptides in electrophoresis gels. In some embodiments, the system of the present invention may operate on a computer platform, such as a local or remote executable software platform, or as a hosted internet or network program or portal. In certain embodiments, only portions of the system may be computer operated, or in other embodiments, the entire system may be computer operated. As contemplated herein, any computing device as would be understood by those skilled in the art may be used with the system, including desktop or mobile devices, laptops, desktops, tablets, smartphones or other wireless digital/cellular phones, televisions or other thin client devices as would be understood by those skilled in the art. The platform is fully capable of being integrated for use with any data recording, analysis, and output procedures as described herein throughout.

The computer platform is fully capable of performing NIRSI and interpreting the imaging results as described herein throughout. For example, the computer platform can be configured to control NIRSI parameters (such as spatial resolution, infrared range, exposure time, and spectral resolution), acquire NIRSI data, interpret the data as images, and subsequently transmit the images to a digital display. The computer platform can also be configured to automatically identify and distinguish all protein bands present on an electrophoresis gel, such that pertinent data is obtained only from the regions of the electrophoresis gel containing protein bands. The computer platform may further perform automated calculations based on the NIRSI recordings to output data such as infrared absorbance, area under the curve, processing of spectra such as calculation of first, second, third, or fourth derivatives, or multivariate analysis, such as partial least squares. The computer platform may further provide a means to communicate the spectral imaging information and data outputs, such as by projecting one or more static and moving images on a screen, presenting one or more digital readouts, and the like.

The computer operable component(s) of the system may reside entirely on a single computing device, or may reside on a central server and run on any number of end-user devices via a communications network. The computing devices may include at least one processor, standard input and output devices, as well as all hardware and software typically found on computing devices for storing data and running programs, and for sending and receiving data over a network, if needed. If a central server is used, it may be one server or, more preferably, a combination of scalable servers, providing functionality as a network mainframe server, a web server, a mail server and central database server, all maintained and managed by an administrator or operator of the system. The computing device(s) may also be connected directly or via a network to remote databases, such as for additional storage backup, and to allow for the communication of files, email, software, and any other data formats between two or more computing devices. There are no limitations to the number, type or connectivity of the databases utilized by the system of the present invention. The communications network can be a wide area network and may be any suitable networked system understood by those having ordinary skill in the art, such as, for example, an open, wide area network (e.g., the internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system.

The system software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a manager, expert, researcher, or other professional of the particular results. Further embodiments of such mechanisms are described elsewhere herein or may standard systems understood by those skilled in the art.

It should be appreciated that the methods of the present invention may be performed using any suitable method of spectroscopy, such as Raman spectroscopy. For example, protein absorbances may be quantified based on Raman scattering, wherein the at least one wavenumber is between 400 cm$^{-1}$ and 4000 cm$^{-1}$.

In some embodiments, the present invention provides a near infrared spectral imaging device for quantifying proteins and peptides in electrophoresis gels. The device may accept electrophoresis gels having protein samples and provide a one-step automated process for quantifying all protein samples on an electrophoresis gel, wherein the NIRSI spectrometer is preprogrammed to identify all protein bands on an electrophoresis gel, acquire the infrared dataset from the electrophoresis gel, generate infrared hyperspectral images from the infrared dataset, calculate area under at least one wavenumber of the infrared spectra for every pixel in the infrared hyperspectral images of each protein band, and quantify the amount of protein in each protein band. In some embodiments, the NIRSI spectrometer may further comprise gel electrophoresis and staining capabilities, such that every step of method 100 or 200 may be performed by a single device. The NIRSI spectrometer may seamlessly perform every step of method 100 or 200 in an automated process without further input from a user. In another embodiment, the present invention provides a Raman spectral imaging device for quantifying proteins and peptides in electrophoresis gels.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out the preferred embodiments of the present invention, and are not to be construed as limiting in any way the remainder of the disclosure.

Example 1: Quantitative Analysis of Gel Electrophoresis Protein Bands Using Near Infrared Imaging Spectroscopy Measurement of protein quantity is an important step in a range of biological procedures, such as new protein identification, pharmaceutical manufacturing, peptide synthesis, and molecular characterization (Noble J E et al., Methods in enzymology 463 (2009): 73-95; Noble J E et al., Molecular biotechnology 37.2 (2007): 99-111). There are several challenges in the process, including measurement of a specific protein in a solution, obtaining adequate measurement precision and sensitivity, and cost and expertise required to assay the protein samples. Various techniques have been developed that are in use for determination of the protein content of a protein solution or solid protein mix (Noble J E et al., Molecular biotechnology 37.2 (2007): 99-111; Olson BJSC et al., Current protocols in protein science (2007): 3-4). Some of these techniques require protein separation or protein enzymatic and biochemical digestion prior to analysis, and some provide a semi quantitative/qualitative approach to protein quantification (Noble J E et al., Methods in enzymology 463 (2009): 73-95; Smith B J, Basic Protein and Peptide Protocols (1994): 107-111).

The most common approaches for protein quantification are based on spectrometric methods that utilize UV/fluorescent absorbance, typically in the range of 220 to 280 nm (Kuipers B J H et al., Journal of agricultural and food chemistry 55.14 (2007): 5445-5451). These techniques can be performed on the original protein solutions with no external contrast added; however, dye-binding alternatives provide more specific results, such as the use of protein-copper chelation (bicinchoninic acid—BCA, and Lowry assays) (Fountoulakis M et al., Journal of biochemical and biophysical methods 24.3-4 (1992): 265-274; Walker J M, Basic protein and peptide protocols (1994): 5-8), and specific dye binding molecules used in the Bradford assay (Bradford M M, Analytical biochemistry 72.1-2 (1976): 248-254). In general, the primary advantage of spectrophotometric techniques is that they are high throughput measurements and use inexpensive reagents. The spectrophotometric quantification process includes generation of a calibration curve using light absorption of protein samples with known amounts of protein, followed by interpolation of protein quantity of the unknown sample on the calibration curve (Simonian M H et al., Current protocols in molecular biology (2006): 10-1). Mathematical models are used to fit to the calibration data, and depending on the accuracy of fit, the interpolation yields concentration information about the protein solution. The major drawback to these techniques is that it's not possible to assess one specific protein within a protein mix. To measure a target protein, it is necessary to first purify the protein mix, generally by a filtering or chromatography process. Microgram amounts of protein can be detected through this method, but assessment of sub-microgram protein amounts are not as reliable (Groves W E et al., Analytical biochemistry 22.2 (1968): 195-210). Further, techniques such as these are challenging to use in combination with gel electrophoresis-based protein separation as the gel material absorbs in the UV range of interest (Noble J E et al., Methods in enzymology 463 (2009): 73-95).

Amino acid analysis can be used for protein quantification, and is considered a gold standard technique since it is based on analysis of individual amino acids in the protein. (Burkitt W I et al., Analytical biochemistry 376.2 (2008): 242-251). This technique includes destructive protein digestion, and is a time consuming and expensive process. Results can be dependent on technician experience, and equipment is not commonly found in most laboratories. Investigators typically send samples to central facilities for evaluation. Since the measurement includes several steps of hydrolysis, derivatization, and then amino acid measurement, it is also vulnerable to error multiplication effects due to issues that may occur in early steps of the process (Olson BJSC et al., Current protocols in protein science (2007): 3-4; Sittampalam G S et al., Journal-Association of official analytical chemists 71.4 (1987): 833-838).

Polyacrylamide gel electrophoresis (PAGE) is frequently used to separate proteins in a protein solution, and is based on protein charge and molecular weight. A protein mix runs through the polymeric gel subjected to an electric field over a certain time chosen to optimize separation. Proteins move through the gel relative to their charge/weight and at the end of the process, their relative positions can be visualized by the additional of an external contrast agent (Issaq H J et al., Biotechniques 44.5 (2008): 697). Blue staining using specific reagents (i.e. Coomassie blue) and silver staining are the most common visualization techniques, and they have been shown to be sensitive in the range of sub-micrograms (Chan J K et al., Analytical biochemistry 226.1 (1995): 191-193; de Moreno M R et al., Journal of pharmaceutical sciences 75.9 (1986): 907-911). Several post-hoc approaches can be taken at this point once proteins are separated. For example, protein gel bands can be excised and hydrolyzed for identification by liquid chromatography tandem mass spectrometry (LC-MS/MS) (Shevchenko A et al., Nature protocols 1.6 (2006): 2856-2860; Domon B et al., Science 312.5771 (2006): 212-217). Protein quantification, however, is usually done using standard light microscopy imaging of the gel combined with densitometry of protein bands (Rabilloud T et al., Journal of proteomics 73.11 (2010): 2064-2077; Berth M et al., Applied microbiology and biotechnology 76.6 (2007): 1223-1243). Since the protein gel bands may not be adequately resolved, especially on the edges, this approach can include relatively large errors and is not usually trusted for precise protein measurements. In addition, not every protein is best suited for quantification in gels. There are side reactions between proteins, gel materials, and staining reagents that can interfere with the measurement process. It has been reported that staining by Coomassie dye can be challenging for dense protein bands, where stain penetration may not be complete (Chan J K et al., Analytical biochemistry 226.1 (1995): 191-193). There are also colorimetric errors where the gel band demonstrates a range of colors in the blue wavelength and computer densitometry results in large errors due to these color variances. Silver staining is also not ideal for measurement of protein quantity in a gel band. Some proteins do not react with a silver stain, the process is very sensitive to the room lighting, there is a high chance of dark gel backgrounds if the gel staining timing is not optimized, and dense protein bands may also suffer from inadequate dye penetration (Noble J E et al., Methods in enzymology 463 (2009): 73-95; Noble J E et al., Molecular biotechnology 37.2 (2007): 99-111). Finally, the addition of contrast that binds to a protein can complicate extraction of the protein from the gel for further quantification (Berth M et al., Applied microbiology and biotechnology 76.6 (2007): 1223-1243). Development of a non-destructive, inexpensive, fast and precise technique to quantify proteins separated by gel electrophoresis would be of great value for applications to protein studies.

The following study presents an application of near infrared spectroscopic imaging (NIRSI) to quantify proteins in electrophoresis gels. Infrared spectroscopic techniques have been used for decades to characterize biological and non-biological samples based on the interaction of the light in the infrared wavelength range with molecules, which augments the vibrations of molecular bonds at characteristic frequencies (Durig J R et al., Infrared and Raman Spectroscopy of Biological Molecules. Springer Netherlands, 1979. 35-43; Koenig J L et al, Applied optics 17.9 (1978): 1374-1385). This vibration-specific absorption provides a precise approach to quantify specific components of a sample including proteins, lipids, water, and glycosylated molecules (Palukuru U P et al., Matrix Biology 38 (2014): 3-11; Boskey A et al., Biomaterials 28.15 (2007): 2465-2478; Baykal D et al., Applied spectroscopy 64.10 (2010): 1160-1166; Hanifi A et al., Osteoarthritis and Cartilage 20.9 (2012): 988-996; Padalkar M V et al., Annals of biomedical engineering 41.11 (2013): 2426-2436; Palukuru U P et al., Analytica chimica acta 926 (2016): 79-87; Homma S et al., Journal of Biomedical Optics 1.4 (1996): 418-424; Afara I O et al., Biomedical optics express 6.1 (2015): 144-154). Infrared spectroscopic evaluations typically span either the mid infrared or near infrared frequencies. Although molecule-specific fundamental vibrations occur in mid-infrared frequencies (400-4000 $cm^{-1}$), the penetration of mid-infrared radiation is limited to ~10 microns, and thus is not suitable for gel protein analysis. Near infrared radiation, in the frequency range of 4000-12000 $cm^{-1}$, however, penetrates deeper into a sample, from mm-cm, depending on the wavelength (or frequency) of interest (Homma S et al., Journal of Biomedical Optics 1.4 (1996): 418-424; Padalkar M V et al., Analyst 140.7 (2015): 2093-2100). The advantages of this modality include a non-destructive, fast, reproducible, quantitative measurement of gel bands, based on intrinsic molecular contrast that is protein specific and sensitive enough to assess protein content in the sub-microgram range (Baykal D et al., Applied spectroscopy 64.10 (2010): 1160-1166; McGoverin C M et al., Annals of biomedical engineering 44.3 (2016): 680-692). In addition, the process can be performed at a specific wavelength that will reduce the analysis time significantly.

The materials and methods are now described.

A calibration-validation approach was performed where calibration curves based on NIRSI of protein solutions with known amounts of protein separated by tris-glycine PAGE were generated. This was followed by prediction of the protein content of a validation set of independent sample solutions with varying amounts of protein separated by tris glycine PAGE and analysis of NIRSI data.

Protein Gel Electrophoresis

Solutions of three proteins with different molecular weights were prepared in purified water. Bovine serum albumin (BSA, molecular weight=67 KDa, Sigma Aldrich, St. Louis, Mo.), lysozyme (molecular weight=14 KDa, Sigma Aldrich, St. Louis, Mo.), and IgG from rabbit serum (molecular weight=150 KDa, Sigma Aldrich, St. Louis, Mo.) were separated through the gel electrophoresis process. Bio-Rad mini-PROTEAN Tetra electrophoresis cell, Bio-Rad universal power supply, and Bio-Rad Bio-Safe Coomassie (Bio-Rad, Hercules, Calif.) were used to run proteins, control time and voltage, and stain protein post-electrophoresis, respectively. Pre-cast 10% Tris-Glycine Extended (TGX) protein gels (Bio-Rad, Hercules, Calif.) with a molecular weight range of 2-200 KDa were used for protein separation. Eight different protein amounts, 10, 20, 50, 100, 200, 500, 1000, and 2000 nanograms, were added to 40 μL of purified water and sample buffer (Laemmli sample buffer, Bio-Rad, Hercules, Calif.) to make eight different solutions for each protein. Proteins were run for 45 minutes at 165V to ensure separation of gel bands. Three gels were run per protein for a total of 27 protein-specific gel bands at 3 bands per concentration per protein. A sample of gel pre-run with no protein, protein gel post-run but pre-staining, and protein gel post-run and after staining, were used in the analysis.

Spectral Data Collection and Processing

Figure 3:
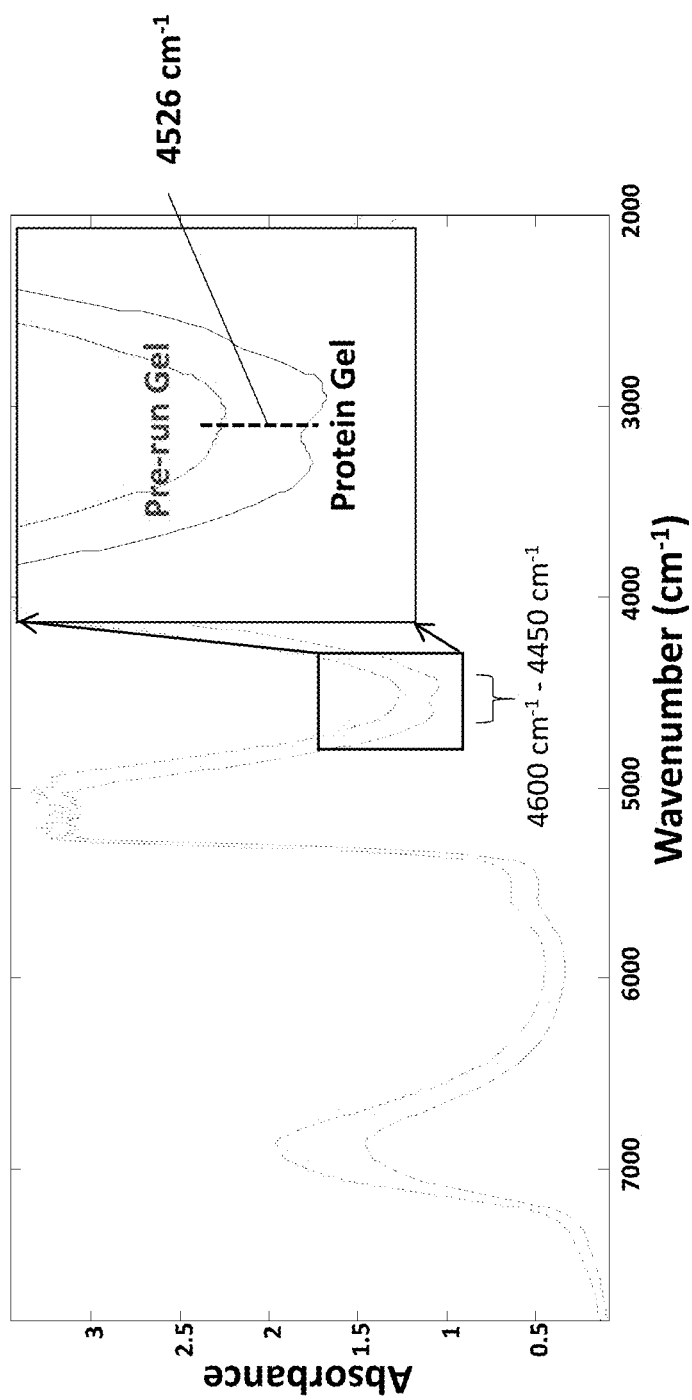
FIG. 3 depicts a NIRSI spectrum of a pre-run gel (no protein, top curve) and a post-run gel (with protein, bottom curve), showing the difference in intensity in the spectral region of 4600 cm$^{-1}$ to 4450 cm$^{-1}$ (inset).
Figures 4A, 4B:
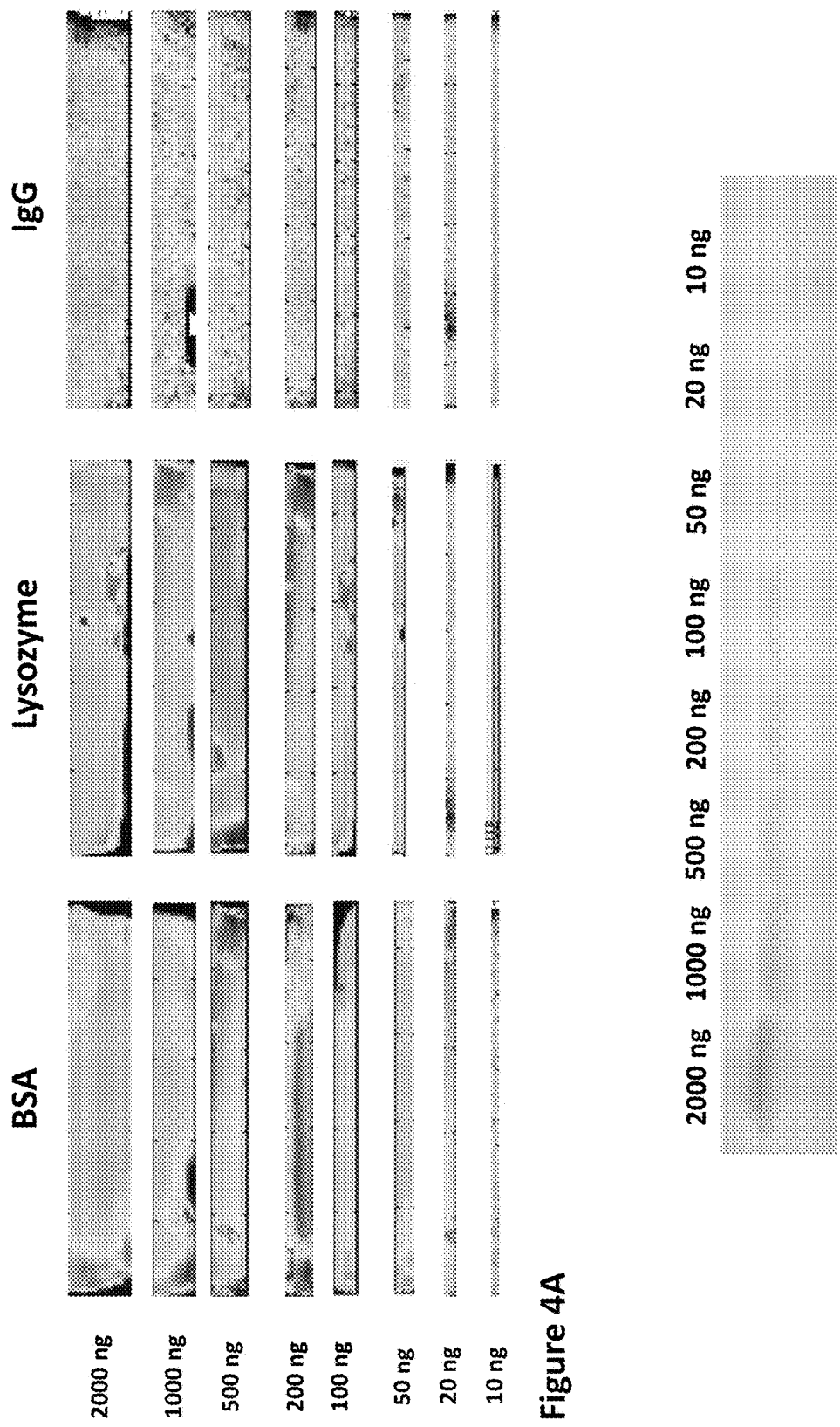
FIG. 4A depicts NIRSI images of 8 different amounts of gel-separated bovine serum albumin (BSA), lysozyme, and IgG protein bands (10 ng to 2000 ng each) based on the integrated area under the wavenumber range between 4600 cm$^{-1}$ and 4450 cm$^{-1}$.
FIG. 4B depicts a BioRad polyacrylamide gel loaded with 8 different amounts of lysozyme protein and stained with Coomassie blue.

Spectral imaging data were collected from regions of the gel using a Spotlight 400 infrared imaging microscope coupled to a Spectrum 100 infrared spectrometer (Perkin Elmer, Waltham, Mass.) in the near infrared frequency range of 8000-4000 $cm^{-1}$. Data were collected in transmittance mode at a spatial resolution of 50 μm and spectral resolution of 16 $cm^{-1}$ with 2 co-added scans. The sample spectra were ratioed to an air background. Scanning of a typical gel band, ~3000 pixels, took 6 minutes. A protein-specific absorbance at frequency 4526 $cm^{-1}$ was present in the protein separated gels, and not in the pre-run gels (FIG. 3). To quantify the total protein content in individual gel bands, NIRSI data were collected from the protein containing gel, and the area under the peak at 4526 $cm^{-1}$ calculated for each pixel (FIG. 4A). The measurement was repeated for each individual protein, BSA, lysozyme, IgG, for the 8 different protein content gel bands. Finally, the total protein content found in each gel band was calculated as the sum of protein absorption at 4526 $cm^{-1}$ at each pixel in the near infrared spectral image.

Calibration Curves and Validation

A calibration curve was created for each protein type separately, i.e, BSA, lysozyme, and IgG, based on the integrated area of the protein absorbance for each concentration. The sum of the integrated area at 4526 $cm^{-1}$ was plotted versus the known protein content (i.e. 10, 20, 50, 100, 200, 500, 1000, and 2000 nanograms). Linear and exponential fits to the curve were investigated. The best model with the highest R2 fit and lowest errors for each protein (one plot for each protein type), and the common optimized model was selected for unknown protein analysis (validation). The common optimized model was defined as the model that yields the highest R2 for the equation type (linear or exponential) that is common among all proteins. NIRSI data from independent protein samples separated on gels with concentrations ranging from 10 to 1500 nanograms were compared to validate the accuracy of the model. Protein specific calibration curves were first used to measure the independent protein content, e.g. the BSA calibration curve was used only for BSA samples, the lysozyme curve was used only for lysozyme samples, and the IgG curve was used only for IgG samples. Subsequently, an analysis was performed where the BSA calibration curve was used to predict the lysozyme and IgG content, to assess whether a universal protein standard, such as BSA, could be used. Infrared spectral image analysis was done using ISys 5.0 software (Malvern Instruments, Worcestershire, UK) and Microsoft Excel was used for the curve fitting analysis.

The results are now described.

Near infrared spectra of protein gel bands (sample) and pre-run electrophoresis gels (control) were used to determine the protein gel band specific infrared absorbance in the near infrared region (FIG. 3). Independent of the type of protein (BSA, lysozyme, or IgG), the gel-containing protein showed a specific absorbance at 4526 $cm^{-1}$ that was not observed in the pre-run gel. This absorbance has been shown to arise from a combination of the NH and OH vibrational modes (Izutsu K et al., Journal of pharmaceutical sciences 95.4 (2006): 781-789).

Figure 5A:
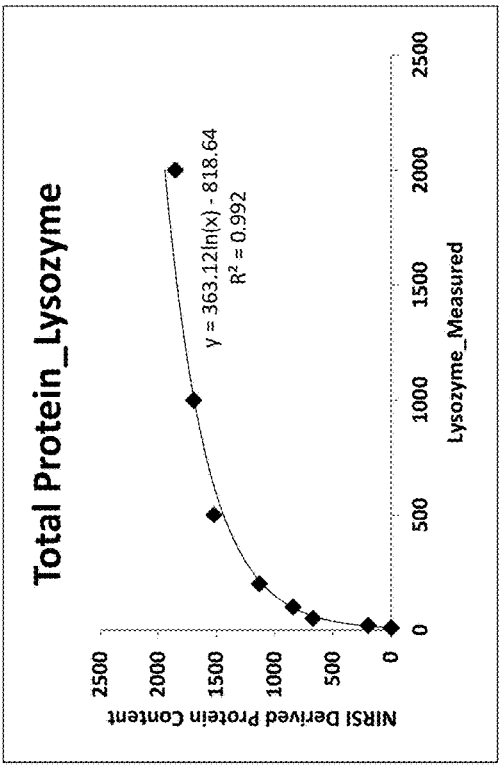
FIG. 5A through FIG. 5C depict regression analyses using results from NIRSI imaging in FIG. 4A for BSA (FIG. 5A), lysozyme (FIG. 5B), and IgG (FIG. 5C).
Figure 5B:
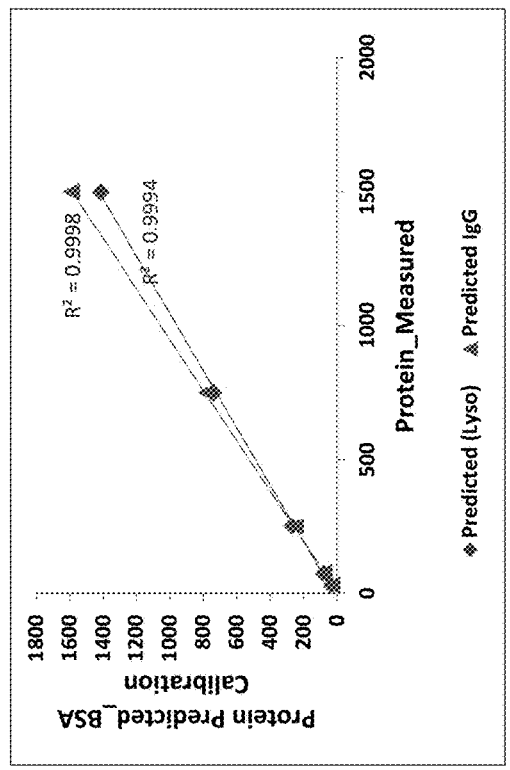
Figure 5C:
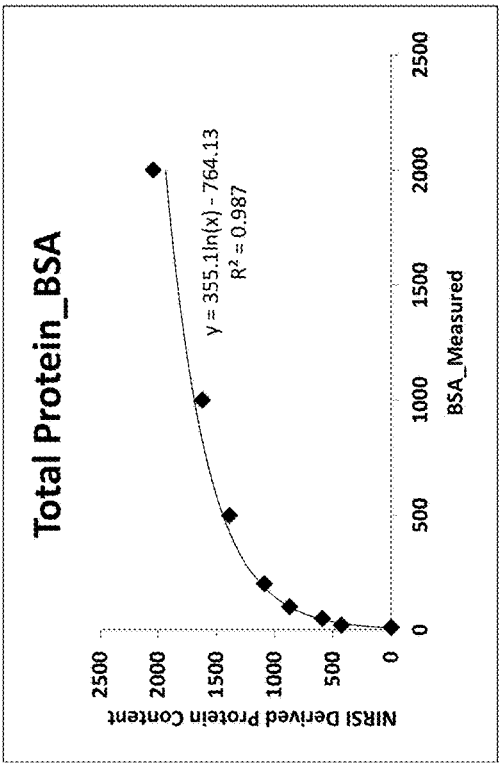
Figure 5D:
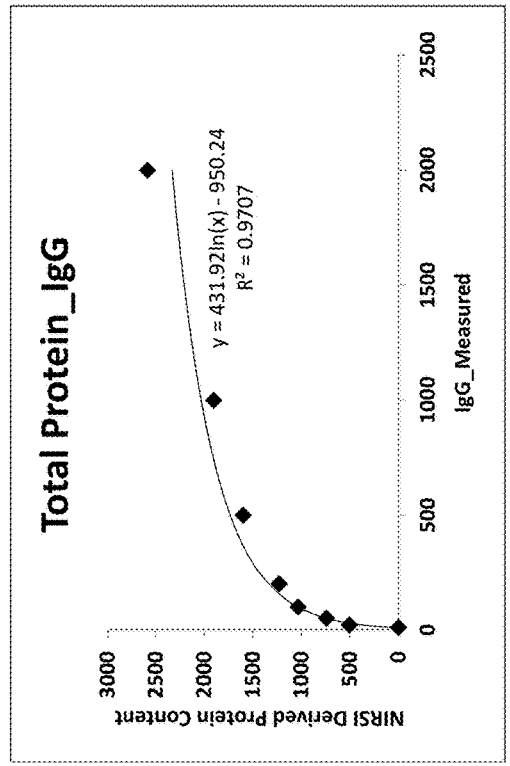
FIG. 5D depicts a graph examining the accuracy of predicting lysozyme and IgG concentration using the BSA calibration curve in FIG. 5A against a sample of measured values of lysozyme and IgG concentration.

Calibration curves for all three protein types were best fit with an exponential curve (FIG. 5A through FIG. 5C). The R2 and (errors) of the calibration curves were 0.98 (7%), 0.99 (4%), and 0.97 (5%), for BSA, lysozyme, and IgG, respectively. The NIRSI data from the set of independent proteins predicted based on the calibration curves resulted in R2 and (errors) of 0.96 (5%), 0.94 (6%), and 0.97 (5%) for BSA, lysozyme, and IgG, respectively. Finally, to investigate the possibility of a universal calibration, the NIRSI-determined quantity of lysozyme and IgG proteins were predicted using the BSA calibration curve. This resulted in R2 and (errors) of 0.99 (7%), and 0.99 (6%), for lysozyme, and IgG, respectively, a 99% agreement with the measured protein content based on the calibration curves of the individual proteins (FIG. 5D).

The expanding number of protein studies in pharmaceutical, diagnostic, and clinical applications, in addition to investigations to identify new proteins, result in an increasing need for reliable techniques to quantify proteins (Noble J E et al., Methods in enzymology 463 (2009): 73-95; Olson BJSC et al., Current protocols in protein science (2007): 3-4; Domon B et al., Science 312.5771 (2006): 212-217). Current techniques provide a range of precision in quantitative analysis, while adding some disadvantages and complications to the process as well. As an example, amino acid analysis is precise, but is destructive, expensive, and time consuming. It can measure total protein content of a solution but does not provide information on the relative amounts of different proteins (Noble J E et al., Molecular biotechnology 37.2 (2007): 99-111; Burkitt W I et al., Analytical biochemistry 376.2 (2008): 242-251). Liquid chromatography mass spectrometry techniques are the most common methods to identify new proteins and can be used to measure protein content at the nanogram level. However, analysis is highly dependent on technician expertise, and is time consuming and expensive (Domon B et al., Science 312.5771 (2006): 212-217). Spectrometry based techniques are simple and easy to use, but to date they typically involve adding reagents to the protein mix, and can result in large errors for assessment of low quantities of protein (Groves W E et al., Analytical biochemistry 22.2 (1968): 195-210). Gel electrophoresis combined with image analysis software provides another approach for protein quantification; however, it can be very inaccurate, especially for thin gel bands, and at the gel band boundaries. This approach also involves adding contrasting reagents that may cause more complications for eventual extraction of the separated protein (Issaq H J et al., Biotechniques 44.5 (2008): 697; de Moreno M R et al., Journal of pharmaceutical sciences 75.9 (1986): 907-911; Rabilloud T et al., Journal of proteomics 73.11 (2010): 2064-2077).

A near infrared spectroscopy technique is proposed in this study as a non-destructive, reliable and easy to use method to quantify proteins separated through the gel electrophoresis process. Infrared spectra have been used widely to assess the composition of different tissue types, based on absorbances specific for protein, sugar, lipid, and genomic material; however, micron penetration depth is a limitation in the mid-infrared spectral region (Palukuru U P et al., Analytica chimica acta 926 (2016): 79-87). Near infrared radiation has been used to evaluate water, sugar, and protein content of engineered and native connective tissues (Palukuru U P et al., Matrix Biology 38 (2014): 3-11; Padalkar M V et al., Annals of biomedical engineering 41.11 (2013): 2426-2436), and is a gold standard method for compositional analysis in the food industry (Huang H et al., Journal of Food Engineering 87.3 (2008): 303-313; Cen H et al., Trends in Food Science & Technology 18.2 (2007): 72-83). Due to its higher penetration depth it provides an ideal option for non-destructive analysis of thick samples, including intact pieces of meat and fish (Huang H et al., Journal of Food Engineering 87.3 (2008): 303-313; Prieto N et al., Meat Science 83.2 (2009): 175-186), and solutions with path lengths of millimeters (Huang H et al., Journal of Food Engineering 87.3 (2008): 303-313). In this work, for the first time, near infrared spectra of protein gel bands demonstrated a protein specific absorbance at 4526 cm$^{-1}$ that is not present in native acrylamide gels. This absorbance was used to generate calibration models and predict protein content of unknown samples. This approach provides a reliable technique for protein quantification without the complications of adding contrasting reagents, destroying the protein molecules, or running complicated additional processes. In addition, it was shown that BSA calibration model is also sensitive to differences in the protein content of other protein types and can be used in simple quantification models when it is difficult to generate unique protein calibration models, or if a new protein is identified. Protein identification and quantification methods offer a range of sensitivity to protein content changes, from 5-10 nanograms for silver staining (Chevallet M et al., Nature protocols 1.4 (2006): 1852-1858) and 30-100 nanograms for coomassie blue staining (Chevallet M et al., Nature protocols 1.4 (2006): 1852-1858) of electrophoresis gels and amino acid analysis, to micrograms in image analysis of protein gel bands and spectrometry analysis of protein solutions (Noble J E et al., Molecular biotechnology 37.2 (2007): 99-111; Burkitt W I et al., Analytical biochemistry 376.2 (2008): 242-251; Sittampalam G S et al., Journal-Association of official analytical chemists 71.4 (1987): 833-838; Shevchenko A et al., Nature protocols 1.6 (2006): 2856-2860). In this study, near infrared analysis accurately assessed the protein quantity from separated protein gel bands containing as little as 10 nanograms. Detection and quantification of small quantities of proteins is one of the biggest challenges of proteomics. Here, near infrared spectral imaging (NIRSI) analysis resulted in accurate measurement of low quantities of protein, and did not require additional contrast or separations.

Example 2: Protein Quantification by Near Infrared Spectral Imaging

Solutions comprising proteins of varying amounts were run on gels using standard electrophoresis methods. Electrophoresis gel containing proteins were imaged using near infrared spectral imaging (NIRSI). The area under the protein specific band located between 4600 cm$^{-1}$ and 4450 cm$^{-1}$ was measured and a distribution map was generated based on the gel NIRSI image. The protein content of each point on the gel (including individual protein bands of standard protein and unknown protein) were calculated. A standard curve was plotted using the standard sample protein content to derive the fit equation (regression analysis). NIRSI absorbance of the unknown protein sample was inputted into the fit equation to evaluate protein content.

Protein samples of 80, 20, 10, 5, 4, 2, 1, 0.5, 0.2, and 0.1 μg (25 μl lysozyme protein solution for each) were loaded onto a pre-cast BioRad polyacrylamide gel (4-20%) using a Biorad mini protein Tetra system. Electrophoresis was run at 165V for 40 minutes. The gel was stained with BioRad Coomassie Blue (G-25) stain to visualize the lysozyme protein bands.

NIRSI was performed on the gel at a pixel resolution of 50 microns in the near infrared spectral range of 8000-4000 cm$^{-1}$ (equivalent to 1250-2500 nm). Each band was imaged in ~5 minutes at a spectral resolution of 16 cm$^{-1}$ with 2 co-added scans per point.

Figure 6:
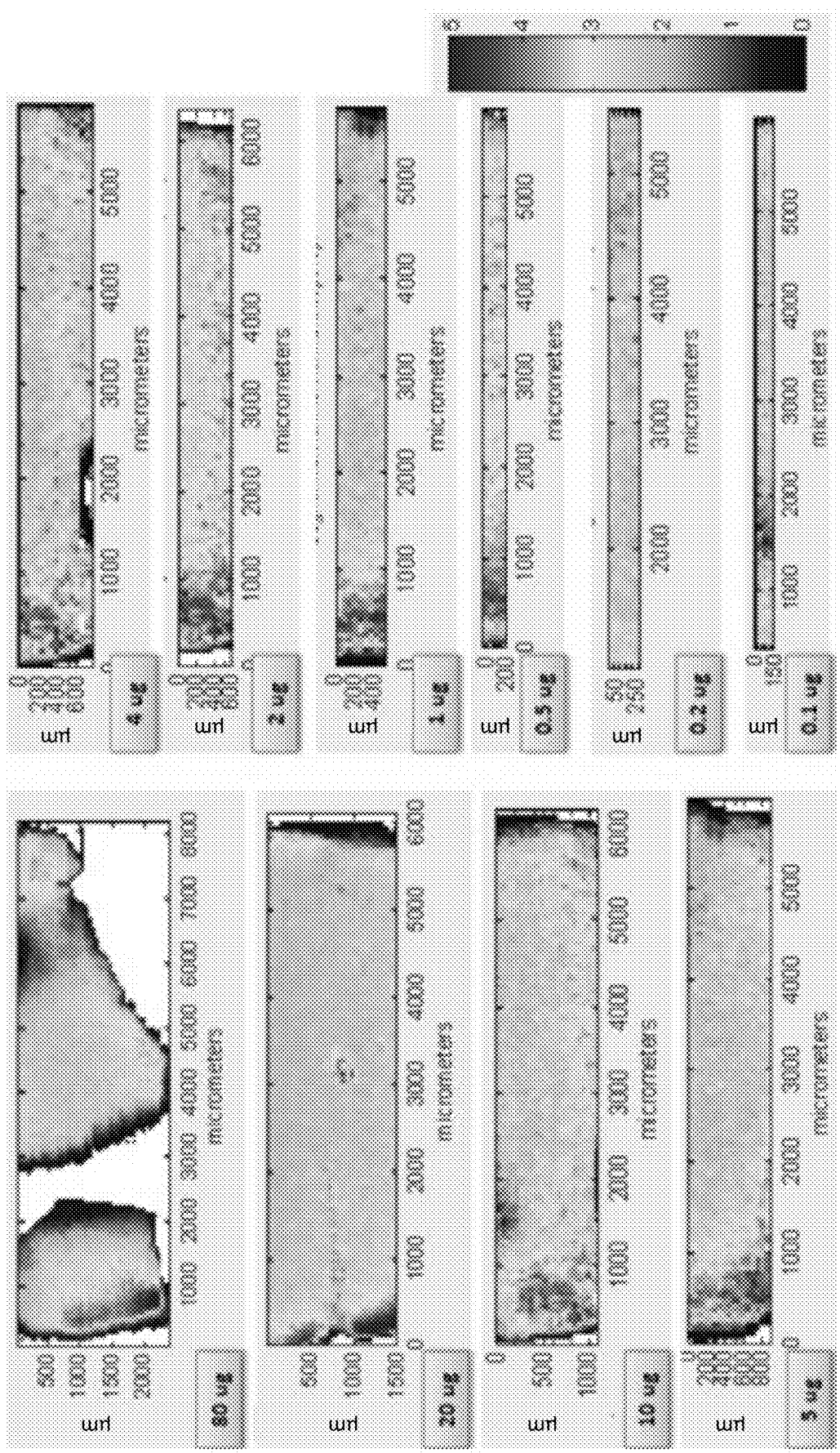
FIG. 6 depicts NIRSI images of different amounts of gel-separated lysozyme protein bands (0.1 to 80 μg) based on the integrated areas under the wavenumber range between 4600 cm$^{-1}$ and 4450 cm$^{-1}$.
Figures 7A, 7B:
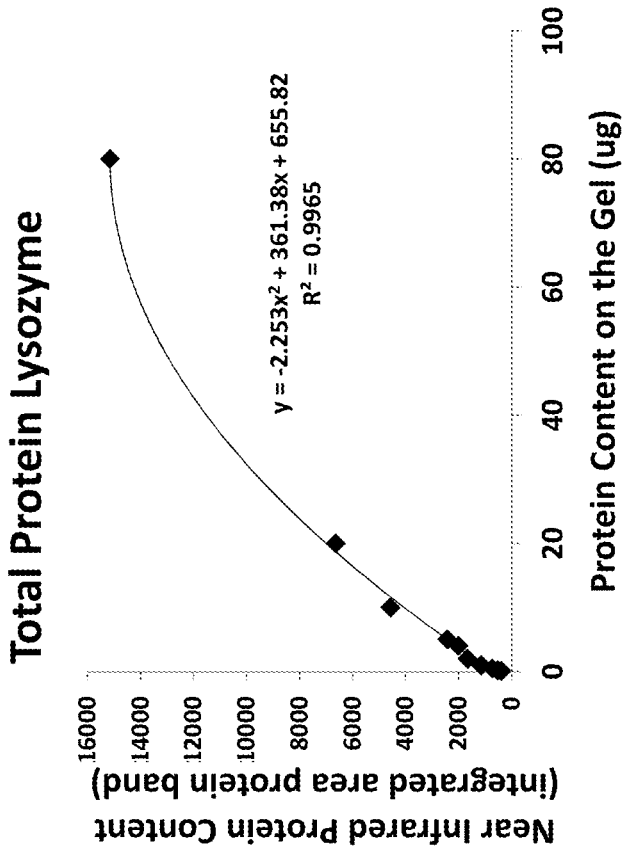
FIG. 7A and FIG. 7B depict depict regression analyses using results from NIRSI imaging of 0.1 to 80 μg lysozyme protein (FIG. 6) and 0.1 to 20 μg of lysozyme protein (FIG. 4A).

NIRSI spectra of the gels with and without protein demonstrated a noticeable difference at the protein specific peak located between 4600 cm$^{-1}$ and 4450 cm$^{-1}$, as expected. The integrated area under the protein peak was measured and a distribution map was generated based on the quantity of the integrated area for gel bands containing different amounts of protein (FIG. 6). The quantity of the sum of the calculated areas under the wavenumber range between 4600 cm$^{-1}$ to 4450 cm$^{-1}$ for every pixel in the infrared hyperspectral image for each protein band was plotted against the nominal protein content to calculate the regression curve (FIG. 7A and FIG. 7B). Regression analysis was used to derive the fit equation to quantify the unknown protein content using the standard curve. The results demonstrate that the R-squared values are over 90% and the NIRSI spectra show a positive correlation to the nominal protein content.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of quantifying protein in an electrophoresis gel, comprising the steps of:
    loading a sample including at least one protein into a gel via electrophoresis to generate at least one protein band;
    acquiring an infrared spectral dataset from the at least one protein band using near infrared spectral imaging (NIRSI);
    generating an infrared hyperspectral image from the infrared spectral dataset for each of the at least one protein band, the infrared hyperspectral image comprising a plurality of pixels;
    calculating the integrated area under at least one wavenumber of the infrared spectrum for every pixel in the infrared hyperspectral image;
    summing the calculated integrated area of every pixel in the infrared hyperspectral image for each of the at least one protein band; and quantifying the amount of protein in the at least one protein band by correlating the sum of the calculated integrated areas with a protein content calibration curve.

2. The method of claim 1, wherein the at least one wavenumber of the infrared spectrum comprises the range between 4600 cm$^{-1}$ and 4450 cm$^{-1}$.

3. The method of claim 1, wherein the at least one wavenumber of the infrared spectrum is selected from 4020 cm$^{-1}$, 4050 cm$^{-1}$, 4260 cm$^{-1}$, 4310 cm$^{-1}$, 4526 cm$^{-1}$, and 4890 cm$^{-1}$.

4. The method of claim 1, wherein the at least wavenumber of the infrared spectrum comprises a range centered at a wavenumber selected from 4020 cm$^{-1}$, 4050 cm$^{-1}$, 4260 cm$^{-1}$, 4310 cm$^{-1}$, 4526 cm$^{-1}$, and 4890 cm$^{-1}$.

5. The method of claim 1, wherein the method comprises obtaining a first, second, third, or fourth derivative of the infrared spectrum.

6. The method of claim 1, wherein the protein content calibration curve is given by the equation $y=2.253x^2+361.38x+655.82$, wherein y is the amount of protein in micrograms and x is the sum of the calculated area under the wavenumber range of the infrared spectra between 4600 cm$^{-1}$ and 4450 cm$^{-1}$ for each pixel of the infrared hyperspectral image acquired from each protein band.

7. The method of claim 1, wherein the protein content calibration curve is given by the equation $y=8.1636x^2+472.37x+485.35$, wherein y is the amount of protein in micrograms and x is the sum of the calculated area under the wavenumber range of the infrared spectra between 4600 cm$^{-1}$ and 4450 cm$^{-1}$ for each pixel of the infrared hyperspectral image acquired from each protein band.

8. The method of claim 1, wherein the protein content calibration curve is given by the equation $y=355.1 \ln(x)-764.13$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band.

9. The method of claim 1, wherein the protein content calibration curve is given by the equation $y=363.12 \ln(x)-818.64$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band.

10. The method of claim 1, wherein the protein content calibration curve is given by the equation $y=431.92 \ln(x)-950.24$, wherein y is the amount of protein in nanograms and x is the sum of the calculated area under the wavenumber range of the infrared spectra between 4600 cm$^{-1}$ and 4450 cm$^{-1}$ for each pixel of the infrared hyperspectral image acquired from each protein band.

11. The method of claim 1, wherein the electrophoresis gel is stained to visualize the at least one protein band using one of a Coomassie Blue stain, a silver stain, a fluorescent stain, and a negative stain.

12. The method of claim 1, wherein the sample of proteins further comprises a calibrant.

13. The method of claim 1, wherein NIRSI is used with a spatial resolution between 1 and 1000 µm.

14. The method of claim 1, wherein the infrared spectrum is recorded in a range between 12000 and 3000 cm$^{-1}$.

15. The method of claim 1, wherein the infrared spectrum is recorded with a spectral resolution between 1 and 100 cm$^{-1}$.

16. The method of claim 1, wherein NIRSI is performed by co-adding and averaging a plurality of scans to improve the signal-to-noise ratio.

17. A method of generating a protein content calibration curve, the method comprising the steps of:
    loading a plurality of protein samples, each sample having a known amount of protein, into a gel via electrophoresis to generate a protein band for each sample;
    acquiring an infrared spectral dataset from each of the protein bands using NIRSI;
    generating an infrared hyperspectral image from the infrared spectral dataset for each of the protein bands, the infrared hyperspectral image comprising a plurality of pixels;
    calculating the integrated area under at least one wavenumber of the infrared spectrum for every pixel in the infrared hyperspectral image;
    summing the calculated integrated area of every pixel in the infrared hyperspectral image for each of the protein bands;
    plotting the known amount of protein in each protein band against the sum of the calculated integrated area for each protein band; and
    generating a line or curve of best fit to create a protein content calibration curve.

18. The method of claim 17, wherein the at least one wavenumber of the infrared spectrum comprises the range between 4600 cm$^{-1}$ and 4450 cm$^{-1}$.

19. The method of claim 17, wherein the at least one wavenumber of the infrared spectrum is selected from 4020 cm$^{-1}$, 4050 cm$^{-1}$, 4260 cm$^{-1}$, 4310 cm$^{-1}$, 4526 cm$^{-1}$, and 4890 cm$^{-1}$.

20. The method of claim 17, wherein the at least wavenumber of the infrared spectrum comprises a range centered at a wavenumber selected from 4020 cm$^{-1}$, 4050 cm$^{-1}$, 4260 cm$^{-1}$, 4310 cm$^{-1}$, 4526 cm$^{-1}$, and 4890 cm$^{-1}$.

21. The method of claim 17, wherein the method comprises obtaining a first, second, third, or fourth derivative of the infrared spectrum.

22. A near infrared spectral imaging device that automatically performs the method of claim 1.

23. The method of claim 1, wherein the spectral imaging is performed using Raman spectral imaging.

* * * * *